United States Patent [19]
Wilson

[11] 4,359,328
[45] Nov. 16, 1982

[54] INVERTED PRESSURE SWING ADSORPTION PROCESS

[75] Inventor: Peter H. Wilson, Findlay, Ohio

[73] Assignee: Union Carbide Corporation, Danbury, Conn.

[21] Appl. No.: 310,038

[22] Filed: Oct. 9, 1981

Related U.S. Application Data

[63] Continuation-in-part of Ser. No. 136,671, Apr. 2, 1980, abandoned.

[51] Int. Cl.$^3$ .............................................. B01D 53/04
[52] U.S. Cl. .......................................... 55/26; 55/58; 55/62; 55/68
[58] Field of Search ................... 55/25, 26, 58, 62, 74, 55/75, 68

[56] References Cited

U.S. PATENT DOCUMENTS

| | | | |
|---|---|---|---|
| 3,085,379 | 4/1963 | Kiyonaga et al. | 55/62 X |
| 3,086,339 | 4/1963 | Skarstrom et al. | 55/26 |
| 3,102,013 | 8/1963 | Skarstrom | 55/62 X |
| 3,142,547 | 7/1964 | Marsh et al. | 55/26 |
| 3,176,444 | 4/1965 | Kiyonaga | 55/26 |
| 3,325,971 | 6/1967 | Rosman | 55/62 |
| 3,564,816 | 2/1971 | Batta | 55/62 X |
| 3,636,679 | 1/1972 | Batta | 55/26 |
| 3,638,398 | 2/1972 | Domine et al. | 55/25 |
| 3,738,087 | 6/1973 | McCombs | 55/62 X |
| 3,797,201 | 3/1974 | Tamura | 55/62 |
| 4,129,424 | 12/1978 | Armond | 55/25 |

FOREIGN PATENT DOCUMENTS 898058 6/1962 United Kingdom .

*Primary Examiner*—Robert H. Spitzer
*Attorney, Agent, or Firm*—Alvin H. Fritschler

[57] ABSTRACT

A gas mixture, having a more readily adsorbable gas component to be recovered and a less readily adsorbable gas component, is introduced to an adsorption zone at low pressure, with the pressure being increased prior to purging the less readily adsorbable gas component from the adsorption zone at high pressure. Upon depressurization, the readily adsorbable gas component is recovered at enhanced purity levels. In multiple adsorption zone operations, each zone is passed through the low pressure adsorption, pressurization, high pressure purging and depressurization cycle, in sequence, with pressure equalization steps advantageously being employed between the zones to be pressurized following adsorption and those being depressurized following purging. The invention can be used to recover nitrogen of enhanced purity from air, and to recover high purity methane from mixtures thereof with nitrogen.

23 Claims, 2 Drawing Figures

INVERTED PRESSURE SWING ADSORPTION PROCESS

CROSS REFERENCE TO RELATED APPLICATION

This application is a continuation-in-part of applicant's copending application entitled "INVERTED PRESSURE SWING ADSORPTION PROCESS", filed Apr. 2, 1980, under Ser. No. 136,671, abandoned.

BACKGROUND OF THE INVENTION

1. Field of the Invention

The invention relates to pressure swing adsorption processes. More particularly, it relates to enhanced recovery of the readily adsorbable component of gas mixtures treated in such processes.

2. Description of the Prior Art

Pressure swing adsorption (PSA) processes, such as PSA-hydrogen, PSA-oxygen and PSA-methane, are commonly carried out by (1) adsorbing the readily adsorbable component of gas mixtures at high component pressure, (2) depressurizing the adsorption zone to effect desorption and an increase in the readily adsorbable component in the gas phase composition at the feed end of the adsorption zone, (3) removing the thus-enriched gas at the feed end of the adsorption zone from said zone by further depressurization or by purging with a purge fluid, and (4) repressurizing the adsorption zone or bed to its original condition. Such removal of the readily adsorbable component results in an accumulation of the less readily adsorbable component in the adsorption zone. This component can be removed from the adsorption zone during the high pressure adsorption step, during the depressurization step or following the purge step.

Enhanced purity of the readily adsorbable component cannot be achieved simply by equilibrating the adsorbent and the feed gas. A purer adsorbed phase can be obtained, however, by incorporating an intensification step after the adsorption step. For this purpose, a so-called copurge gas, constituting a pure gas having essentially the same composition as the readily adsorbable component, is introduced to the adsorption zone or bed at substantially the same pressure as is employed in the adsorption step. The pure readily adsorbable component displaces the less readily adsorbable component from the adsorption bed, thus resulting in a purer adsorbed phase and enhanced purity of the readily adsorbable component recovered upon desorption at a reduced pressure. Such an approach is described in the Tamura patent, U.S. Pat. No. 3,797,201, which discloses the use of recycled, readily adsorbable component for the copurge step carried out at the adsorption pressure. The amount of said recycled component, repressurized from low pressure product, constitutes a significant operating cost associated with this approach.

Another approach involving adsorption, copurge and desorption is described in the British Pat. No. 858,059. In the process of this patent, a molecular sieve is used to adsorb normally liquid, readily adsorbable components from mixtures thereof with less readily adsorbable components. A copurge step is carried out under conditions such that substantially the only normally liquid, readily adsorbable components remaining in contact with the sieve at the end of the copurge step are those adsorbed in the initial adsorption step. Such normally liquid, readily adsorbed components are then desorbed and recovered. The purging step is carried out by passing a normally gaseous material, such as isobutane and preferably nitrogen, over the molecular sieve. The purging step serves to remove non-adsorbed and surface-adsorbed material substantially without desorbing the readily adsorbable, normally liquid material from within the pores of the sieve. Purging conditions are said to be selected to reduce the tendency for material to be desorbed from within said pores, and include (1) the use of temperatures not higher than that employed in the adsorption step, (2) elevated pressure up to 150 p.s.i.g., with adsorption pressures of 0–150 p.s.i.g., preferably 50–100 p.s.i.g., and purging pressures of 0–150 p.s.i.g., preferably 0 p.s.i.g., being disclosed, or (3) reduced pressure, i.e. vacuum purging again preferably at a temperature not exceeding that of the adsorption step and for short periods not longer than that of the adsorption step. While this process is disclosed as providing improvements in the separation of straight chain hydrocarbons from mixtures thereof with branched and/or cyclic hydrocarbons, it does not relate directly to the separation of readily and less readily adsorbable components of normally gaseous mixtures, such as the separation of nitrogen from oxygen and the separation of methane from mixtures thereof with nitrogen. The requirement of copurging with a separate, normally gaseous material likewise adds to the overall cost and complexity of the process.

There remains, therefore, a need in the art for improvements in pressure swing adsorption processes for the separation of the readily adsorbable components of gas mixtures from the less readily adsorbable components thereof. Such improvements are particularly needed for use in pressure swing adsorption applications in which it is desired to recover the readily adsorbable component at enhanced purity levels. While PSA processes are normally employed to optimize the purity level of the less readily adsorbable component, some improvement in the purity level of the recovered readily adsorbable component can be achieved provided that the purity restriction for the less readily adsorbable component is removed. The PSA processes have been unable, however, to achieve desirable high purity levels for the readily adsorbable component despite efforts to optmize such levels within the scope of conventional processing. For example, a conventional PSA air separation process normally used to produce high purity oxygen, i.e. the less readily adsorbable component, has been found to produce nitrogen, the readily adsorbable component, at a purity level of about 86% using a particular adsorbent in a particular, 3-bed system. When this system is optimized for nitrogen recovery, it has been found that the nitrogen purity is increased to about 88%. The conventional process is unable to achieve enhanced nitrogen recovery, however, as to recover nitrogen at purity levels in excess of 95%.

The desired improvements in pressure swing adsorption processes, enabling the readily adsorbable component to be recovered at enhanced purity levels, would enable reasonably pure nitrogen or other inert gases to be produced in locations or applications where conventional inert gas generators or cryogenic air separation units are not suitable. For example, locations on board trucks or aircraft or ships, or applications involving small and/or intermittent use are not suited for inert gas production by conventional means. In addition, a need exists for a process for producing high Btu methane gas from mixtures thereof with low Btu nitrogen in natural gas wells that would be competitive with available cryogenic methods.

It is an object of the present invention, therefore, to provide an improved pressure swing adsorption process.

It is another object of the invention to provide a pressure swing adsorption process for the enhanced recovery of the readily adsorbable component of a feed gas mixture.

It is another object of the invention to provide a pressure swing adsorption process for the recovery of nitrogen of enhanced purity from air.

It is another object of the invention to provide a pressure swing adsorption process for the recovery of methane of enhanced purity from mixtures of methane and nitrogen.

With these and other objects in mind, the invention is hereinafter described in detail, the novel features thereof being pointed out in the appended claims.

SUMMARY OF THE INVENTION

The invention utilizes a pressurization step, following adsorption to cause selective adsorption of the readily adsorbable component of a gas mixture and enrichment of the gas phase in the less readily adsorbable gas component. The adsorption column is then purged at high pressure with the readily adsorbable component, the above-indicated enrichment facilitating the purging operation so that less purge gas is required than in the known approach as discussed above with respect to the Tamura patent. Upon depressurization of the adsorption column, readily adsorbable gas component is released from the adsorbent and can conveniently be recovered from the adsorption zone as a desireable product to enhance purity. The inverted pressure swing adsorption of the invention is advantageously carried out in two or more columns each of which passes through the (1) low pressure adsorption, (2) pressurization to high pressure, (3) purging at said high pressure, and (4) depressurization for release of the readily adsorbable component cycle. In multiple column operation of the invention, pressure equalization is desirably employed to equalize the pressure in a bed to be depressurized with the pressure in a bed or beds to be pressurized and purged as intermediate processing steps enhancing the overall inverted pressure swing adsorption process of the invention.

BRIEF DESCRIPTION OF THE DRAWINGS

The invention is hereinafter further described with reference to the accompanying drawings in which.

DETAILED DESCRIPTION OF THE INVENTION

Figure 1:
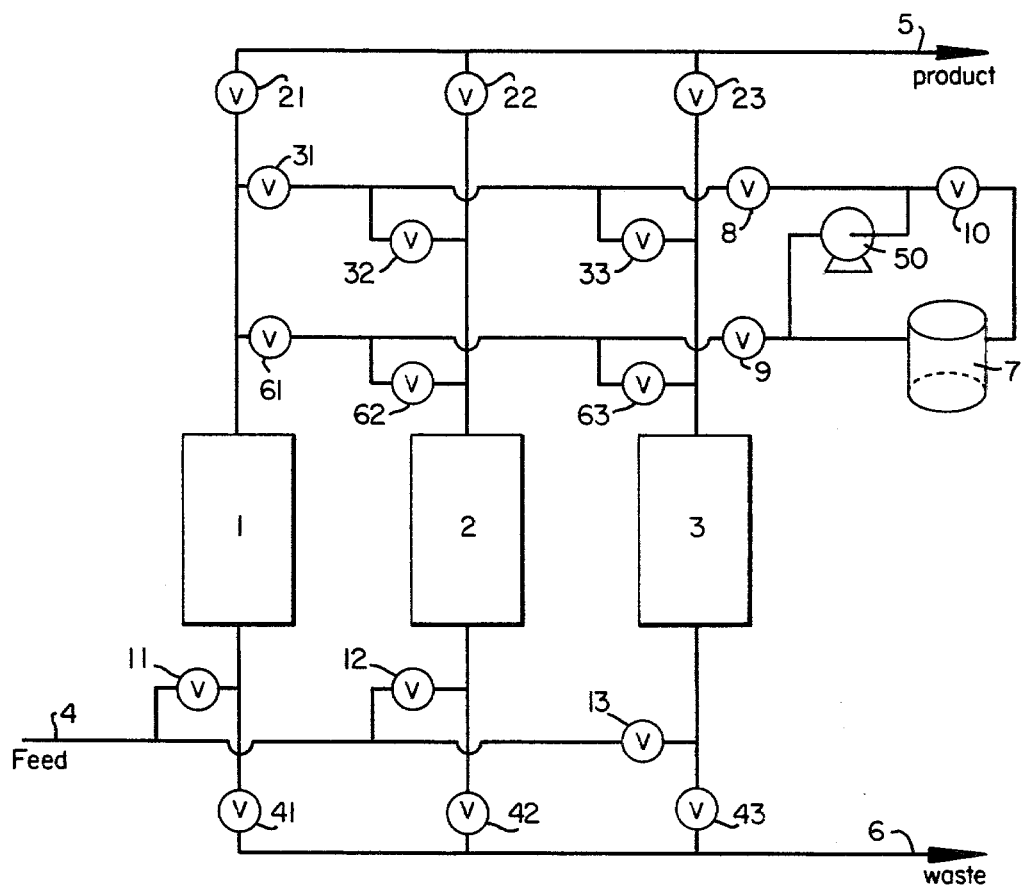
FIG. 1 is a schematic representation of a three adsorption column system adapted for use in the practice of a desirable embodiment of the invention.

The objects of the invention are accomplished by the employing of an inverted pressure swing adsorption process facilitating the removal of the less readily adsorbable component during the purging step and enhancing the purity of the readily adsorbable component recovered as high purity gas product. The typical prior art PSA processes employ (1) adsorption at high pressure, (2) depressurization, (3) enriched waste, i.e. impure readily adsorbable or heavy component removal at low pressure, and (4) repressurization, with the product being the less readily adsorbable or light component. The product can be removed from the adsorption bed during one of several steps, such as during the adsorption step at high pressure, as part of the depressurization step or after a purge step. By contrast, the inverted PSA process of the invention employs (1) adsorption at low pressure, (2) pressurization, (3) enriched waste, i.e., impure less readily adsorbable or light component, removal at high pressure, and (4) depressurization with release of the readily adsorbable or heavy component at low pressure as the desired product of enhanced purity. In the low pressure adsorption of step (1) of the invention, the less readily adsorbable gas component of the gas mixture is adsorbed since it is at a higher component (or partial) pressure than the pressure of said component in the bed initially and after each depressurization step of the cyclic process. The less readily adsorbable gas component of the gas mixture thus displaces and depletes the more readily adsorbable gas component in the adsorbed phase on the adsorbent. As a result, an advancing gas phase zone of the more readily adsorbable gas component precedes a gas phase zone containing both readily and less readily adsorbable gas components. Increasing the pressure in the adsorption zone, in step (2) of the invention, causes the selective adsorption of the readily adsorbable gas component. This results in the depletion of the readily adsorbable gas component in the gas phase and in the corresponding enrichment of the gas phase in the less readily adsorbable gas component. The purging of the adsorption zone with the readily adsorbable gas component, in step (3), serves to remove the gas phase enriched in the less readily adsorbable gas component from the adsorption zone. The depressurization of the adsorption zone in step (4) results, therefore, in the release of the readily adsorbable gas component from the adsorbent at an enhanced purity level compared with that achievable in conventional PSA processing operations.

Conventional PSA processes, even upon removal of the purity requirements for the less readily adsorbable component and optimization for improved purity of the readily adsorbable component, have been able to achieve only a very limited increase in the purity level of readily adsorbable component. Significant improvements in such purity level is readily obtainable, however, by the practice of the inverted PSA process of the process. By the incorporation of a pressurization step, increasing the pressure in the adsorption column from a lower pressure to a higher pressure, an enrichment of the less readily adsorbable or light component in the gas phase is achieved, with a further depletion of the readily adsorbable or heavy component in the gas phase as a result of additional selective adsorption of said component by the adsorbent. Because of the enrichment of the less readily adsorbable component in the gas phase, less of the readily adsorbable gas component is required for use as copurge gas for the enriched waste, i.e. impure less readily adsorbable or light component, removal at high pressure. This is an important operating advantage over conventional PSA processes in which more of the readily adsorbable component is required to remove the less enriched gas phase from the adsorption zone or column. The pressurization step, following low pressure adsorption and preceding the desorption of readily adsorbable component from the adsorbent, serves to decrease the amount of the less readily adsorbable component in the adsorbed phase and to enrich the gas phase therein. This gas phase is advantageously removed by purging at high pressure with the readily adsorbable component, after which a release of a significantly purer, readily adsorbable component results from the depressurization step of the invention.

The invention can be practiced in a simple adsorption column system or alternately by the use of at least two adsorption columns each containing a bed of adsorbent. It will be readily appreciated that the particular composition of the adsorbent employed does not form an essential feature of the present invention. Those skilled in the art are readily aware of PSA processes in general and of the commerical availability of adsorbents capable of selectively adsorbing the readily adsorbable gas component therefrom. In the Tamura patent referred to above, for example, silica gel, activated carbon and zeolite are disclosed for such purpose, together with a naturally occurring tuff consisting mainly of $SiO_2$, $Al_2O_3$ and water containing 1-10 weight percent of alkali and alkaline earth metal oxides. It should likewise be noted that the terms "readily adsorbable component" and "less readily adsorbable component" of a gas mixture should not be construed as implying that the invention is limited to the separation of two component mixtures. One important application of the invention, as noted, involves the recovery of the readily adsorbable component, i.e. nitrogen, of enhanced purity from air consisting primarily of nitrogen and oxygen Another important application resides in the enhanced recovery of readily adsorbable components, i.e. methane and ethane, from gas mixtures containing such components and nitrogen as the less readily adsorbable component in natural gas wells. The readily adsorbable component and/or the less readily adsorbable component may actually comprise two or more component materials within the scope of the invention.

The readily adsorbable gas component released upon depressurization can be conveniently removed from the column as product gas of enhanced purity. The product gas can, for example, be purged from the column. The readily adsorbable gas can be employed as purge gas to remove the released, readily adsorbable gas component from the adsorption column as product gas. In another embodiment, the readily adsorbable gas component released upon depressurization can be removed from the column as product gas upon further introduction of the feed gas mixture to the column. For the purposes of the invention, the adsorption column is conveniently pressurized to the high pressure following low pressure adsorption by introducing additional quantities of the readily adsorbable gas component to said column.

In embodiments in which the gas mixture is introduced to at least two adsorption columns each containing a bed of suitable adsorbent, the inverted pressure swing adsorption cycle of low pressure adsorption, pressurization, purging at high pressure and depressurization for release of the readily adsorbable component, is carried out in sequence in each bed. When the process is carried out in a three bed system, the feed gas mixture is conveniently introduced into only one of the beds at any given time. One bed thus has the gas mixture introduced therein for the adsorption portion of the cycle, a second bed undergoes pressurization and purging during that time, and the third bed undergoes depressurization during that time in a desirable embodiment of the invention. The inverted pressure swing adsorption process continues, in this embodiment, with the three beds switching roles so that the bed previously undergoing adsorption is then employed for pressurization and high pressure purge, the bed previously undergoing pressurization and purge is then employed for depressurization, and the bed previously undergoing depressurization is then employed for adsorption. In a further preferred embodiment of the three bed system, the pressure in the second and third beds are equalized during adsorption in the first bed. For this purpose, gas is passed from the bed to be depressurized into the bed to the pressurized and purged, prior to further pressurization of one bed to the high pressure and to further depressurization of the other bed to low pressure for adsorption. This achieves desirable operating efficiencies as will be readily apparent to those skilled in the art.

In desirable embodiments of the four bed, inverted PSA system of the invention, the feed gas mixture is introduced into only one of the adsorption beds at any given time, with each bed, in sequence, passing through the inverted PSA cycle as described above. The beds will be understood to switch roles so that the bed previously undergoing adsorption at low pressure is then employed for pressurization to high pressure, the bed previously undergoing pressurization is employed for purging at high pressure, the bed previously employed for purging is depressurized to low pressure, and the bed previously depressurized is employed for low pressure adsorption of the less readily adsorbed gas component from additional quantities of the gas mixture. This is possible since the less readily adsorbed component is at a higher component (or partial) pressure than the component pressure in the bed just depressurized. It is advantageous, in such embodiments, to equalize the pressure between the bed having previously undergone low pressure adsorption and a bed being depressurized by passing gas from said bed being depressurized into said bed to be pressurized, prior to further depressurization of said bed being depressurized to said low pressure. In a separate, subsequent step, further equalization of the pressure between the bed to be pressurized and the next bed being depressurized following high pressure purge is desirably achieved by passing high pressure gas from the next bed being depressurized into the bed being pressurized prior to further equalization and depressurization of the bed being depressurized to the low pressure for adsorption and further pressurization of the bed being pressurized to the high pressure. In such desirable embodiments, each bed in turn undergoes two pressure equalization steps prior to final depressurization to low pressure.

The invention is capable of achieving enhanced purity levels of the readily adsorbable component beyond those obtainable by optimization of conventional PSA processes. The invention can thus be employed to produce nitrogen product gas having a purity of at least about 95% from air. Likewise, the invention can recover, from natural gas mixtures of methane, ethane and nitrogen having a low heating value of on the order of about 750 BTU/SCF, a product gas comprising methane and ethane of enhanced purity having a heating value of on the order of about 1,100 BTU/SCF (i.e. standard cubic foot). As illustrated in the examples, the invention can conveniently be carried out for nitrogen recovery from air using a low pressure of essentially atmospheric pressure for adsorption, with pressurization to a high pressure of about 35 psig, with equalization to an intermediate pressure of about 15 psig being used in the three bed system. In a four bed system for methane and ethane recovery from mixtures with nitrogen, a low pressure of essentially atmospheric pressure is again convenient, with a high pressure of about 50 psig and equalization pressures of about 30 psig and about 13 psig being convenient in a particular application. Those skilled in the art will readily appreciate that the particular low pressure for adsorption, high pressure for purging and intermediate equalization pressures in multiple bed systems can be varied depending upon the requirements of any given application, including the desired balance between the purity levels required and operating costs and any other factors that may be pertinent to a given application for the enhanced recovery of the readily adsorbable component.

As indicated above, the conventional PSA approach did not permit the achieving of high purity of the readily adsorbed component. The storage of the less readily adsorbed component, e.g., oxygen in an air separation process, could not be decreased sufficiently prior to the desorption of the readily adsorbed component from the adsorption bed. The maximum purity of the product containing the readily adsorbable component, e.g., nitrogen in air separation, was thereby limited. Even upon removal of the purity restriction on the oxygen product and optimization to increase the nitrogen purity, it has not been possible to decrease the quantity of oxygen on the nitrogen product to acceptable levels for high purity nitrogen. For example, comparative runs were made using a conventional 3 bed PSA system with 13×8×12 adsorbent beads for air separation purposes. When optimized for less readily adsorbable component, i.e., oxygen, purity and recovery, the more readily adsorbable component, i.e. nitrogen, was recovered at a purity level of 86% with total recovery in excess of 99%. When the system was optimized for nitrogen, the nitrogen purity obtained was increased only to 88% at a nitrogen recovery of less than 99%.

In the FIG. 1 embodiment of the invention, three adsorbent beds numbered 1, 2 and 3 are used to separate feed air consisting primarily of oxygen and nitrogen to recover nitrogen at purities above about 95%. In the first step, feed air in line 4 passes through valve 11 into bed 1. Nitrogen rich product is withdrawn from bed 1 through valve 21 and exists through line 5. Additionally, bed 3 depressurizes into bed 2 through valves 33 and 32, thus transferring nitrogen-rich gas. At the completion of this step, beds 2 and 3 are equalized in pressure. In the second step, feed air continues to enter bed 1 through valve 11. Valves 21, 33 and 10 are closed, while valves 61, 9, 8 and 32 are opened. Nitrogen-rich gas is withdrawn from bed 1 through valves 61 and 9 and is compressed by product gas compresser 50 to repressurize bed 2 to high pressure through valves 8 and 32. Simultaneously in step 2, nitrogen-rich product is withdrawn from bed 3 through valve 23 as bed 3 depressurizes from its first equalization pressure to a lower equalization pressure. In the third step, valve 42 opened. Feed air continues to enter bed 1, while nitrogen-rich gas is withdrawn from the product end of bed 1 and is compressed by compressor 50 and enters bed 2 through valve 32. Bed 2 is purged at high pressure, while oxygen-enriched waste is withdrawn through valve 42 and line 6. Bed 3 continues to provide product nitrogen through valve 23 and depressurizes to low pressure for subsequent adsorption. Step 4 is a repeat of step 1 with bed 3 now receiving feed gas, and bed 2 depressurizing into bed 1. The inverted PSA cycle continues with the three adsorbent beds switching roles until step 10, which is identical with step 1 upon completion of the operating sequence in which each bed, on a cyclic basis, is subjected to low pressure adsorption, pressurization, high pressure purging and depressurization, with intermediate pressure equalization steps. Valve 10 is opened to allow compresser 50 to operate unloaded during steps 1, 4 and 7 when compresser draws no process gas. It will be understood by those skilled in the art that valves 22, 31, 62, 63, 12, 13, 41, and 43 shown on the drawing serve to permit operation of the inverted PSA process, in the manner described with respect to steps in the overall sequence subsequent to the low pressure adsorption in bed 1 particularly described above. A gas surge drum is shown by the numeral 7. The overall cycle sequence for the three bed, inverted PSA system as described above is schematically represented in Table 1 as follows:

TABLE 1

| Bed | Operating Step | | | | | | | | |
|---|---|---|---|---|---|---|---|---|---|
| | 1 | 2 | 3 | 4 | 5 | 6 | 7 | 8 | 9 |
| 1. | ADS | ADS | ADS | EQUAL | REP | PURGE | EQUAL | DEP | DEP |
| 2. | EQUAL | REP | PURGE | EQUAL | DEP | DEP | ADS | ADS | ADS |
| 3. | EQUAL | DEP | DEP | ADS | ADS | ADS | EQUAL | REP | PURGE | where ADS represents low pressure adsorption, EQUAL represents pressure equalization, REP represents repressurization, PURGE represents high pressure purge with the readily adsorbable component, and DEP represents depressurization.

EXAMPLE 1

In an illustrative example using the inverted PSA system of FIG. 1 as described above, air separation was accomplished using 13×8×12 adsorbent beads at a bed weight of 20 weight units, with the feed air rate being 100 volume units and the product nitrogen rate being 25 volume units. At the completion of step 1, bed 5, 2 and 3 were both at a pressure of 15 psig, beds 1 and 2 initially being at atmospheric pressure with bed 3 being at 35 psig. In the second step, bed 2 is repressurized to 35 psig, with bed 3 being depressurized from 15 to 8 psig. In the third step, bed 2 is purged at constant 35 psig pressure, and bed 3 depressurizes to atmospheric pressure. In such operation of invention, nitrogen, the readily adsorbable component, is recovered at a nitrogen recovery of 31.5%, the purity of the nitrogen product being enhanced to a 96% product purity level.

Figure 2:
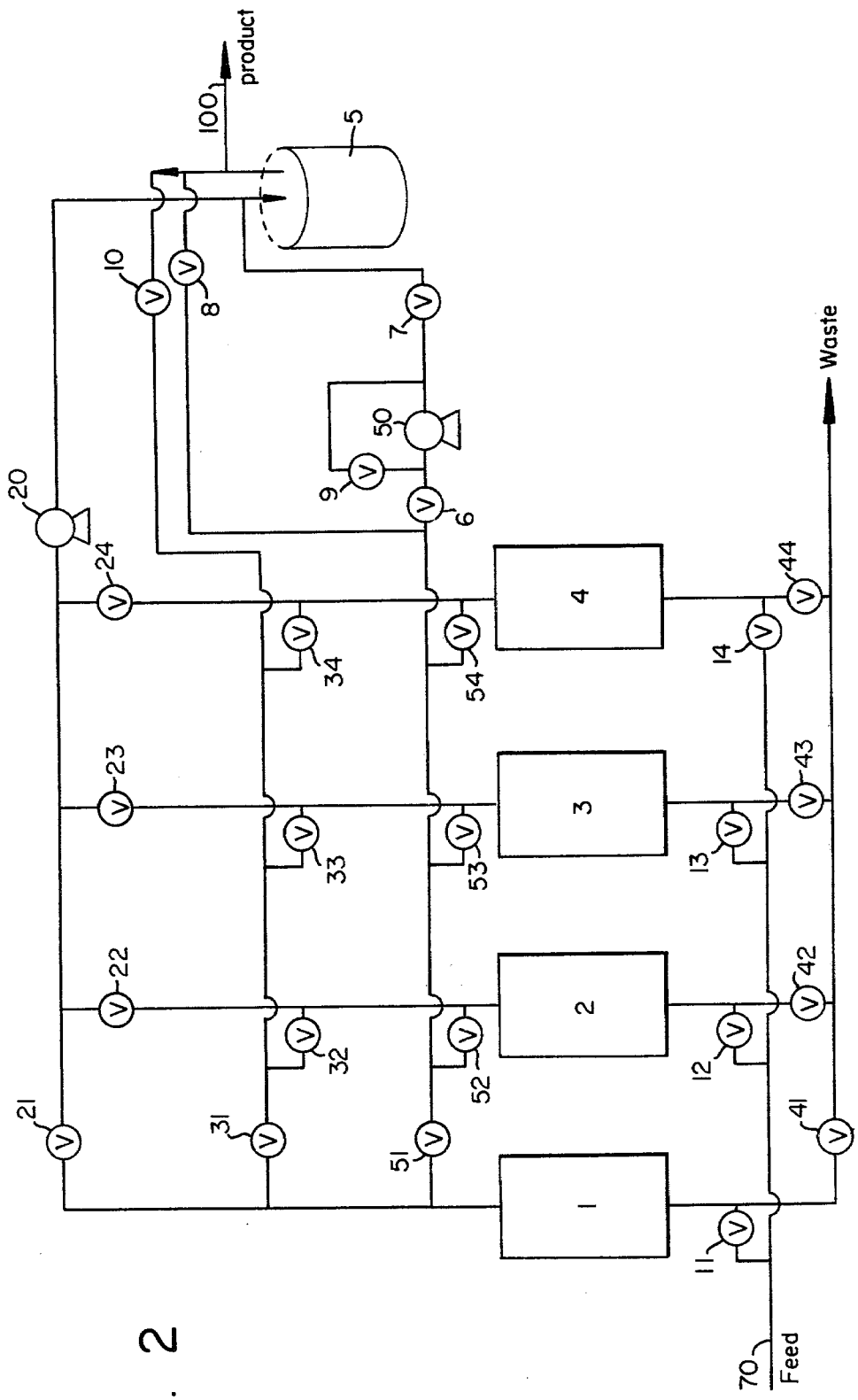
FIG. 2 is a schematic representation of a four adsorption column system adapted for use in the practice of the invention.

FIG. 2 represents a four adsorbent bed embodiment of the inverted PSA system. The four adsorbent beds, numbered 1, 2, 3 and 4, are to recover the readily adsorbable methane and ethane from the less readily adsorbable nitrogen in a feed gas mixture of such components. Two compressors, numbered 50 and 20, and product surge tank 5 are incorporated in the system. In steps 1, 4 and 7 of the process summarized in Table 2 below, valve 9 is opened and valves 6, 7 and 10 are closed to allow compressor 50 to operate unloaded.

Initially, beds 1, 2, 3, and 4 are at low pressure, a higher intermediate pressure, low pressure, and said higher intermediate pressure, repectively. At the start of step 1, feed gas enters bed 1 from line 70 at low pressure through valve 11, and hydrocarbon-rich gas exits from bed 1 through valve 21. This gas is compressed in compressor 20 and fills product surge tank 5. Some of the gas is withdrawn as product though line 100, while some of this material passes through valves 8 and 52 and repressurizes bed 2 to the high pressure for purging. Bed 4 depressurizes through valves 34 and 33 into bed 3 until the pressures equalize at a lower intermediate pressure. In step 2, feed gas still enters bed 1 through valve 11, exits from the top thereof through valve 21, is compressed in compressor 20, enters surge tank 5, and is partially withdrawn as hydrocarbon-rich product through line 100. Bed 4 depressurizes through valves 54 and 6 to a low pressure. This gas is compressed in compressor 50 and passes through valve 7 into the surge drum 5, with valves 8 and 9 being closed. Gas exits from surge tank 5 through valves 10 and 32 to the top of bed 2. Valve 42 is open, allowing bed 2 to be purged at high pressure. Bed 3 is completely isolated at this time. In step 3, as in step 2, bed 1 is on low pressure adsorption with gas flowing through valves 11 and 21, through compressor 20, and into surge drum 5. Beds 2 and 3 undergo pressure equalization through valves 32 and 33, valve 10 being closed. The final pressure of beds 2 and 3 following such equalization is the higher intermediate pressure. Bed 4 depressurizes to low pressure through valve 54, with the gas passing through valve 6, compressor 50, valve 7 and into surge tank 5. Step 4 is a repeat of step 1 with bed 1 equalizing in pressure with bed 2, with bed 3 repressurizing, and bed 4 undergoing low pressure adsorption. The inverted PSA cycle continues with the four beds switching roles until step 13, which is identical with step 1 upon completion of the operating sequence in which each of the four beds, on a cyclic basis, is subjected to low pressure adsorption, pressurization, high pressure purging and depressurization, with intermediate pressure equalization steps at two pressure levels. It will be understood by those skilled in the art that elements identified in FIG. 2 but not described with respect to steps 1—3, e.g., valves 14, 24, 44, 51 and 53 are employed in subsequent steps of the overall process as the four beds and related transport lines and valves switch roles so that each bed passes through the recited steps of the inverted PSA process of the invention. The overall cycle sequence for the four bed embodiment of the invention described above is schematically represented in Table 2 as follows:

TABLE 2

| Bed | Step 1 | 2 | 3 | 4 | 5 | 6 | 7 | 8 | 9 | 10 | 11 | 12 |
|---|---|---|---|---|---|---|---|---|---|---|---|---|
| 1. | A | A | A | Eq2 ↑ | — | Eq1 ↑ | R | P | Eq1 ↓ | Eq2 ↓ | D | D |
| 2. | R | P | Eq1 ↓ | Eq2 ↓ | D | D | A | A | A | Eq2 ↑ | — | Eq1 ↑ |
| 3. | Eq2 ↑ | — | Eq1 ↑ | R | P | Eq1 ↓ | Eq2 ↓ | D | D | A | A | A |
| 4. | Eq2 ↓ | D | D | A | A | A | Eq2 ↑ | — | Eq1 ↑ | R | P | Eq1 ↓ | where A represents low pressure adsorbtion; Eq represent pressure equalization, with the number 2 indicating the lower intermediate pressure and the number 1 indicating the higher equalization pressure, with an upward arrow indicating the pressure is being increased, and a downward arrow indicating the pressure is being decreased, during said equalization; R represents repressurization to the high pressure; P represents purging with the readily adsorbable component; and D represents depressurization to low pressure for subsequent adsorption.

EXAMPLE 2

The inverted PSA system as shown in FIG. 2 employed in an illustrative example in which readily adsorbable methane and ethane were separated from nitrogen in a feed mixture of said components. JXC activated carbon 8×12 adsorbent beads were employed at a bed weight of 20 weight units per bed. The feed composition was 36% nitrogen, 57% methane and 7% ethane, having a heating value of 738 BTU/SCF. The feed rate was 115 volume units, and the product rate was 15 volume units. Initially, beds 1, 2, 3, and 4 were at pressures of 0, 30, 0 and 30 psig, respectively. During this step, bed 2 was repressurized to a high pressure of 50 psig, bed 1 being operated at atmospheric pressure as the low pressure for adsorption. Bed 4 depressurized into bed 3 until the pressures were equalized at 13 psig, i.e. the lower intermediate pressure, said 30 psig being the upper intermediate pressure in this illustrative example. In step 2, bed 4 depressurized to a low pressure of 2 psig. Bed 2 was purged at said 50 psig. In step 3, the final equalization pressure of beds 2 and 3 was 30 psig. Bed 4 depressurized to atmospheric pressure. As a result of this illustrative practice of inverted PSA process of the invention, the product gas recovered had a product composition of 69.4% methane, 21.6% ethane and only 9% nitrogen. Hydrocarbon recovery was 64.3%, with the product heating value having been raised to 1080 BTU/SCF.

Those skilled in the art will appreciate that various changes and modifications can be made in the practice of the invention as described with respect to specific applications in the examples, or as more generally described in the specification, without departing from the scope of the invention as set forth in the claims. Thus, the particular pressures employed, the particular commercially available adsorbent employed, and the quantity thereof, the number of beds employed and the like will all vary from application to application, depending on the particular feed gas composition, the desired purity of the readily adsorbable component, the purity restrictions that may remain with respect to the less readily adsorbable component and the general balancing of purity improvement and operating costs referred to above.

The invention represents a very significant development in the PSA art. By providing a means to achieve enhanced purity of the readily adsorbable component of a gas mixture, the inverted PSA process herein disclosed and claimed overcomes a deficiency in the art that can not be overcome by optimizing the conventional PSA units for enhanced purity of the readily adsorbable component. This enables nitrogen or like inert gases to be conveniently produced by the pressure swing adsorption approach at purity levels suitable for applications on board trucks, aircraft or ships where conventional inert gas generators or cryogenic air separation units are not suitable. The inverted PSA process of the invention is also particularly suited for small and/or intermittent uses where alternate approaches are not suitable. In the production of high Btu methane or methane-ethane mixtures from natural gas wells, the process of the invention achieves such conversion to higher energy fuels as to enable the inverted PSA approach to compete favorably with less desirable cryogenic techniques. The invention thus is of potential commercial value in a range of practical applications, based on its ability to enhance the purity levels for the readily adsorbable component of gas mixtures commonly subjected to separation in major industrial operations.

What is claimed is:

1. A cyclic inverted pressure swing adsorption process for enhancing the purity of the readily adsorbable gas component recovered from a gas mixture of said gas component with a less readily adsorbable gas component comprising:
   (a) introducing said gas mixture at a first, low pressure to an adsorption column containing an adsorbent capable of selectively adsorbing the readily adsorbable gas component therefrom, the less readily adsorbable gas component of the mixture being adsorbed at said low pressure, displacing and depleting the more readily adsorbable gas component in the adsorbed phase, resulting in an advancing gas phase zone of said readily adsorbable gas component preceding a gas phase zone containing both readily and less readily adsorbable gas components;
   (b) increasing the pressure in said column to a second, high pressure causing selective adsorption of the readily adsorbable gas component, thereby depleting said component in the gas phase and enriching said gas phase in the less readily adsorbable gas component;
   (c) purging the column with said readily adsorbable gas component at said high pressure to remove said gas phase enriched in the less readily adsorbable gas component from said column;
   (d) depressurizing said column from said high pressure, the depressurization resulting in a release of the readily adsorbable gas component from the adsorbent; and
   (e) repeating said steps (a)-(d) on a cyclic basis with additional quantities of said gas mixture,
whereby the inverted pressure swing adsorption cycle results in an increased adsorption of the more readily adsorbable gas component by the adsorbent at high pressure and increased separation of said component from the less readily adsorbable gas component at said high pressure, enhancing the purity of said readily adsorbable gas component recovered upon depressurization of the column following the convenient purging of the less readily adsorbable gas component therefrom.

2. The process of claim 1 in which said gas mixture comprises air, said readily adsorbable gas component being nitrogen and said less readily adsorbable gas component being oxygen.

3. The process of claim 1 in which said gas mixture comprises nitrogen and methane, said readily adsorbable gas component being methane and said less readily adsorbable component being nitrogen.

4. The process of claim 1 and including removing said readily adsorbable gas component released upon depressurization from said column as product gas of enhanced purity.

5. The process of claim 4 which said readily adsorbable gas component released upon depressurization is purged from said column.

6. The process of claim 5 in which the readily adsorbable gas component is employed as purge gas to remove said released, readily adsorbable gas component from the column as product gas.

7. The process of claim 1 and including removing said readily adsorbable gas component released upon depressurization from said column as product gas upon the further introduction of said gas mixture to the column.

8. The process of claim 1 in which the column is pressurized to said high pressure by introducing additional quantities of the readily adsorbable gas component to said column.

9. The process of claim 1 in which said gas mixture is introduced to at least two adsorption columns each containing a bed of said adsorbent, the inverted pressure swing adsorption cycle of adsorption at low pressure, purging at said high pressure and depressurization for release of the readily adsorbable component being carried out in sequence in each bed.

10. The process of claim 9 in which said inverted pressure swing adsorption cycle is carried out in a three bed system, with the gas mixture being introduced into only one of said beds at any given time, one bed thus having the gas mixture introduced therein for the adsorption portion of the cycle, a second bed undergoing pressurization and purging during said time, and a third bed undergoing depressurization during said time, said inverted pressure swing adsorption process continuing with the three beds switching roles so that the bed previously undergoing adsorption is then employed for pressurization and high pressure purge, the bed previously undergoing pressurization and purge is then employed for depressurization, and the bed previously undergoing depressurization is them employed for adsorption.

11. The process of claim 10 and including, during adsorption in one bed, equalizing the pressure in the second and third beds by passing gas from the bed to be depressurized into the bed to be pressurized and purged, prior to further pressurization of the second bed to said high pressure and to further depressurization of said third bed to said low pressure.

12. The process of claim 11 in which said gas mixture comprises air, said readily adsorbable gas component being nitrogen and said less readily adsorbable gas component being oxygen.

13. The process of claim 11 in which said gas mixture comprises nitrogen and methane, said readily adsorbed gas component being nitrogen.

14. The process of claim 9 in which said inverted pressure swing adsorption cycle is carried out in a four bed system, with the gas mixture being introduced into only one of said beds at any given time, each bed, on a cyclic basis, having the gas mixture introduced therein for the adsorption of the less readily adsorbable component at said low pressure, being pressurized to said high pressure, being purged at said high pressure, and being depressurized to said low pressure, with the beds switching roles so that the bed previously undergoing adsorption is then employed for pressurization to high pressure, the bed previously undergoing pressurization is employed for purging at high pressure, the bed previously employed for purging is depressurized to low pressure, and the bed previously depressurized is employed for low pressure adsorption of the readily adsorbed gas component from additional quantities of the gas mixture.

15. The process of claim 14 and including, during adsorption in one bed, equalizing the pressure between the bed having previously undergone adsorption at low pressure and a bed being depressurized by passing gas from said bed being depressurized into said bed to be pressurized prior to further depressurization of said bed being depressurized to said low pressure, and in a separate subsequent step, further equalizing the pressure between said bed to be pressurized and the next bed being depressurized following high pressure purge by passing high pressure gas from said next bed being depressurized into said bed being pressurized, prior to further equalization and depressurization of the bed being depressurized to said low pressure and further pressurization of said bed being pressurized to said high pressure, each bed in turn undergoing two pressure equalization steps prior to final depressurization to low pressure.

16. The process of claim 15 in which said gas mixture comprises air, said readily adsorbable gas component being nitrogen and said less readily adsorbable component being oxygen.

17. The process of claim 15 in which said gas mixture comprises nitrogen, methane and ethane, said readily adsorbable gas components being methane and ethane, and said less readily adsorbable component being nitrogen.

18. The process of claim 12 and including removing said nitrogen, released upon depressurization, from said system as a product gas of enhanced purity.

19. The process of claim 18 in which said nitrogen product gas has a purity of at least about 95%.

20. The process of claim 17 and including recovering methane and ethane, released upon depressurization, from said system as a product gas of enhanced purity.

21. The process of claim 20 in which the gas mixture has a low heating value of on the order of about 750 BTU/SCF and said product gas of enhanced purity has a heating value of in the order of about 1100 BTU/SCF.

22. The process of claim 18 in which said low pressure is essentially atmospheric pressure, said high pressure is about 35 psig and said equalization pressure is about 15 psig.

23. The process of claim 20 in which said low pressure is essentially atmospheric pressure, said high pressure is about 50 psig and said equalization pressures are about 30 psig and about 13 psig.

* * * * *